United States Patent [19]

Berry, Jr.

[11] Patent Number: 4,558,585
[45] Date of Patent: Dec. 17, 1985

[54] ULTRASONIC ANGLE BEAM STANDARD REFLECTOR

[75] Inventor: Robert F. Berry, Jr., Hayes, Va.

[73] Assignee: The United States of America as represented by the Administrator of the National Aeronautics and Space Administration, Washington, D.C.

[21] Appl. No.: 590,921

[22] Filed: Mar. 19, 1984

[51] Int. Cl.[4] ...................... G01N 29/04; G01D 18/00
[52] U.S. Cl. ..................... 73/1 DV; 72/341; 72/324
[58] Field of Search ............... 73/1 DV; 72/324, 340, 72/341; 264/DIG. 66, 319

[56] References Cited

U.S. PATENT DOCUMENTS

| | | | |
|---|---|---|---|
| Re. 14,835 | 6/1920 | Giebel et al. | 72/340 |
| 2,826,940 | 3/1958 | Smith | 72/340 |
| 3,608,352 | 9/1971 | Walton et al. | 73/1 DV X |
| 3,677,061 | 7/1972 | Visser | 73/1 DV X |
| 3,898,944 | 8/1975 | Holk, Jr. et al. | 72/341 |
| 3,908,439 | 9/1975 | Pelak . | |
| 3,933,026 | 1/1976 | Henn et al. . | |
| 4,106,326 | 8/1978 | Lather et al. | 73/1 DV |
| 4,173,139 | 11/1979 | Conn | 73/1 DV |
| 4,182,154 | 1/1980 | Lather et al. | 73/1 DV |
| 4,203,315 | 5/1980 | Vien et al. . | |
| 4,445,360 | 5/1984 | Treder, Jr. | 73/1 DV |

FOREIGN PATENT DOCUMENTS

| | | | |
|---|---|---|---|
| 2852752 | 7/1979 | Fed. Rep. of Germany | 73/1 DV |
| 425102 | 4/1975 | U.S.S.R. | 73/1 DV |

Primary Examiner—Jerry W. Myracle
Assistant Examiner—Tom Noland
Attorney, Agent, or Firm—Howard J. Osborn; John R. Manning; Wallace J. Nelson

[57] ABSTRACT

This invention is a method for providing an impression profile in a reference standard material utilized in inspecting critically stressed components with pulsed ultrasound. A die stamp (10) having an I letter, reference numeral (36), is used to impress a reference material (50) having a surface (52). The die stamp is placed against the surface (52) and struck with an inertia imparting member to impress the I in the reference standard material. Upset (54) may appear on the surface (52) as a result of the impression and is removed to form a smooth surface (52). The stamping and upset removal is repeated until the entire surface area of a depth control platform (30) on the die stamp uniformly contacts the material surface (52). The I impression profile in the reference standard material (50) is utilized for reflecting pulsed ultrasonic beams as a means for inspecting ultrasonically.

11 Claims, 8 Drawing Figures

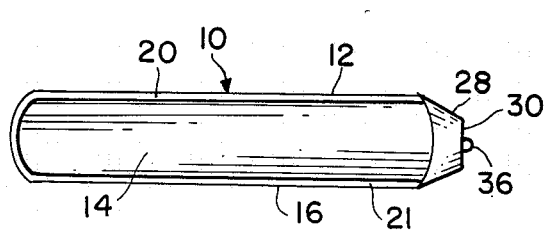
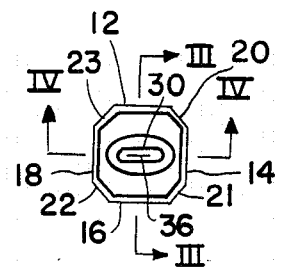
FIG. 1
FIG. 2
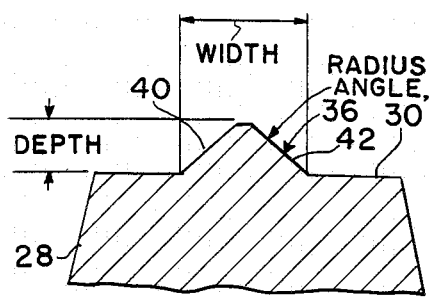
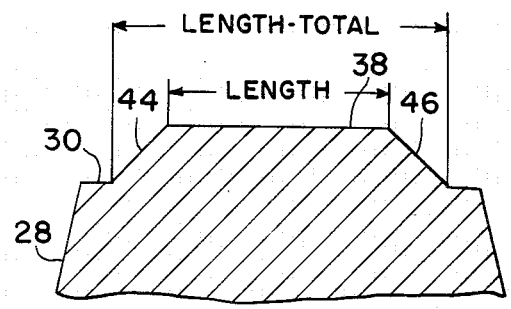
FIG. 3
FIG. 4
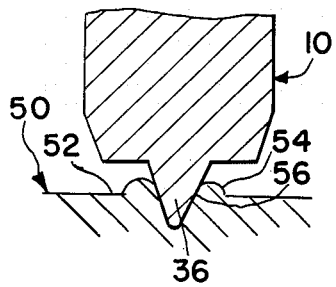
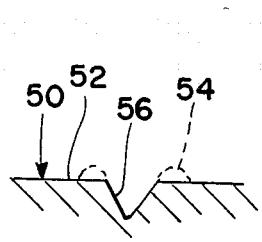
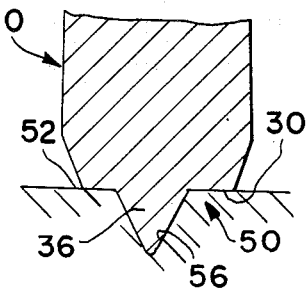
FIG. 5
FIG. 6
FIG. 7
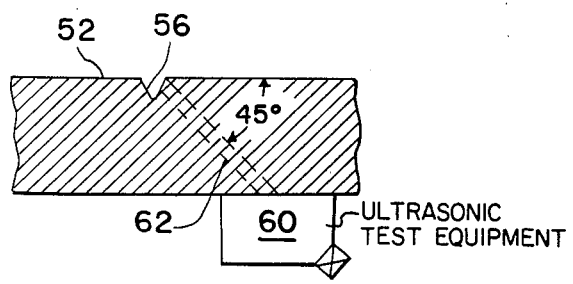
FIG. 8

ULTRASONIC ANGLE BEAM STANDARD REFLECTOR

ORIGIN OF THE INVENTION

The invention described herein was made by an employee of the U.S. Government and may be manufactured and used by or for the Government for governmental purposes without the payment of any royalties thereon or therefor.

BACKGROUND OF THE INVENTION

The use of ultrasonic equipment for detecting flaws in metal parts, as well as certain non-metallic parts, such as composites, is known in the prior art. When pulsed ultrasonic sound waves generated by a transducer or other mechanism are transmitted into a part to be inspected, internal defects or flaws, as for example, a crack, voids or other discontinuities in the part, will cause a portion of the sound wave impinging on the defect to be reflected back toward the transducer or other receiving mechanism. The time interval between the transmission of the sound pulse into the material being inspected and when the pulse reflected from the defect reaches the transducer is a measure of the distance between the point where the ultrasonic wave enters or leaves the body and the location of the defect. Also, magnitude of the reflected pulse is a measure of the size of the defect as viewed in the direction of travel of the sound waves.

Such ultrasonic test equipment is calibrated by using holes, v-notches, or half-circle profiles which are drilled or otherwise machined in test blocks or the material being tested. One such machining technique is that of a electric discharge machine the operation of which involves considerable time and expense. These profiles are drilled or machined to different depths to form surfaces which reflect sound waves entering the test block or material being tested. For a test standard the inspector usually works with profiles of one size and different depths. The ultrasonic test equipment is calibrated by transmitting sound pulses into each of these profiles. This way the data obtained from the calibrated blocks can be used to determine the size of flaws and the depth of flaws within the material being tested by the equipment. The profiles of different sizes and depths can also be placed in the material being tested to obtain similar information.

Considerable difficulty has been experienced in the past with drilling or machining of the profiles so as to provide a surface at the bottom and edge of each which is not only parallel or at the right angle to the surface of the block from which the ultrasonic sound beam is transmitted into the block, but also is truly flat so as to provide a reflecting surface of the desired area facing the path of travel of the sound beam. Also, with the prior art profile forming techniques, it is difficult to obtain the same surface finish at the bottom or edge of each profile in order that these surfaces have essentially the same reflective characteristics to sound beams.

In view of the above enumerated difficulties of forming an impression in a material which can be used as a reference standard, it is an object of this invention to provide a method of forming an impression profile in the material which does not require drilling.

It is yet another object of this invention to provide a method for forming an impression profile in a material which can be used as a reference standard which does not require other expensive and time consuming machining processes such as the use of an electric discharge machine.

Yet another object of this invention is to provide a method for forming an impression profile in a material standard by the use of a die stamp.

Still another object of this invention is to provide a method for forming an impression profile in a material standard wherein the profile takes the shape of the letter I.

Another object of the invention is to provide a method for forming an impression profile in a material standard wherein the impression has consistent repeatability when impressed in various materials used for standards.

A further object of the invention is to provide a method for various classes of inspection by varying the dimensions of the die stamp, and thereby the sizes of the impressions made in the material standard.

Another object of the invention is to provide a method for forming an impression profile in a material standard with the use of hand tools.

SUMMARY OF THE INVENTION

The foregoing and other objects of the invention are achieved by providing a commercially available die stamp which is of high quality. Preferably the die stamp embodies the letter I which will be utilized to impress this profile in the reference standard material. The die stamp is placed against the material and struck with a mallet or other inertia imparting object to form an impression in the material. Any upset which might appear on the surface of the material being impressed is removed by filing or some other technique. The die stamp is then again placed in the impression and the above procedure repeated until the depth control platform of the die stamp uniformly contacts the material surface. This procedure results in a quick and inexpensive method of impressing a profile which is of uniform design in the reference standard material. Various classes of inspection can be accomplished by varying the size of the die stamp which will vary the size of the impression profile ultimately placed in the reference standard material.

Other advantages and objects of the invention will become apparent from the following explanation of an exemplary procedure and accompanying drawings.

BRIEF DESCRIPTION OF THE DRAWINGS

FIG. 1 is a side elevational view of a die stamp used in performing the method of the invention;

FIG. 2 is an end view of a die stamp used in performing the method of the invention;

FIG. 3 is a cross-sectional view of the die stamp taken along the section lines III—III of FIG. 2;

FIG. 4 is a cross-sectional view of the die stamp taken along the section lines IV—IV of FIG. 2;

FIG. 5 is an elevational view in cross-section showing the initial impression by a die stamp in a reference standard material;

FIG. 6 is an elevational view in cross-section of the reference standard material showing the upset on the surface in dotted lines indicating material which must be removed;

FIG. 7 is an elevational view in cross-section showing the die stamp bottomed on the reference standard material and the final shape of the impression profile; and FIG. 8 is an elevational view, showing the standard reference material in cross-section to reveal the impression profile, and a diagrammatical view of ultrasonic equipment bouncing sound waves off the impression.

DETAILED DESCRIPTION OF THE INVENTION

The die stamp utilized in forming the impression profile in the reference standard material is best shown in FIG. 1, and is designated generally by the reference numberal 10.

The die stamp 10 has a handle 12 which is essentially square with flat sides 12, 14, 16 and 18. The corners are beveled to form bevels 20, 22, 21 and 23 for ease in gripping the handle. Obviously, the handle can take other shapes such as round or octagon to accomplish the purpose of securely holding the die stamp in the users hand.

The head of the die stamp has a taper 28, which tapers to the depth control platform 30. The depth control platform 30 is perpendicular to the longitudinal dimension of the handle, and is a flat surface which is oval in shape as viewed in FIG. 2. The dimension of the depth control platform is of a nature such that the surface area thereof when contacting the reference standard material to be impressed, will provide a uniform impression of the die stamp letter when it completely contacts or bottoms on the reference material surface.

The die stamp letter body 36 is positioned in the center of the depth control platform 30. It has been found in utilizing the method that the die stamp I is a preferred shape, since it provides essentially a v-groove impression in the reference standard material. The I-body has sides 40 and 42 which are positioned at 90° with respect to the depth control platform 30 i.e. the sides intersect, or would intersect, at a 90° angle and has the radius 38 which varies between 0.001 inch and 0.002 inch depending on the depth or height of the letter I. The radius 38 is that of the rounded contacting tip portion of the die stamp. The letter I can be designed to have various dimensions depending on the class of inspection being made, to be explained more fully hereinafter. The ends of the I-body, 44 and 46 are also positioned at approximately 90° with respect to the depth control platform 30. The following table provides detailed dimensions for various letter sizes utilized in accomplishing the method of the invention.

TABLE

| LETTER 1 SIZE | 1/16" | ⅛" | 3/16" |
| --- | --- | --- | --- |
| Angle | 90° | 90° | 90° |
| Radius | .001 inch | .001 inch | .002 inch |
| Depth | .016 inch | .030 inch | .035 inch |
| Width | .032 inch | .060 inch | .070 inch |
| Length | .064 inch | .125 inch | .190 inch |
| Length Total | .096 inch | .185 inch | .260 inch |

Although it should be understood that other die stamps might be utilized, it has been found that steel die stamps bearing the letter I as manufactured by Young Brothers Stamp Works, Inc., Muscatine, Iowa are of the quality and workmanship to accomplish the purpose of the invention.

OPERATIONAL STEPS OF THE METHOD OF THE INVENTION

The die stamp 10 is utilized in the following manner to accomplish the method of the invention.

The letter I, reference numeral 36, is placed against the reference standard material, which bears the reference numeral 50 in FIG. 5. The end of the die stamp 10 is struck with an object such as a mallet or other inertia imparting device. The die stamp will impress the surface 52 of the reference standard material forming an impression profile 56. Usually after the first blow by the mallet, the reference standard material surface 52 will be upset to form a raised ridge which is shown in FIGS. 5 and 6 and designated by the reference numeral 54. The upset 54 is shown in dotted line in FIG. 6 to indicate that this material is removed from the surface 52 by any conventional method such as filing with a file which will remove steel or whatever material the reference standard material may consist of. Obviously, other techniques may be used for removing the upset.

When the upset 54 has been removed, the die stamp I-body 36 is then placed in the impression 56, and the die stamp again struck with a mallet to further impress the reference standard material. Any upset is again filed off. The above procedure is repeated until the depth control platform 30 uniformly contacts the material surface 52, as shown in FIG. 7. It should be understood, that if the above procedure is followed in each instance, the I-body 36 of the die stamp will provide an impression profile 56 which is of uniform design in each instance providing the necessary standard impression profile needed for proper ultrasound inspection.

FIG. 8 shows the reference standard material 50 with the proper impression profile 56 impressed therein. Ultrasonic equipment 60 directs a beam 62 onto the profile 56 at an optimum 45° angle for angle beam detection. The reflected beam 62 is analyzed and compared by the test equipment 60 in a manner generally similar to that described in the operation of ultrasonic testing equipment set forth above in the description of the Background of the Invention. Various commercially available pulsed ultrasonic test instruments are available, and a detailed description of the operation of this equipment is not believed necessary for the understanding of the method of this invention.

In specific use of the method of this invention, three class areas of angle beam inspection were utilized as a standard, and are set forth herein for purposes of better understanding how the particular method is utilized.

For Class I, discontinuity indications in excess of the response from a 1/16 inch high letter I stamp at the estimated depth shall not be acceptable, and discontinuity indications in excess of 50% of the response from a 1/16 inch high letter I die stamp (50% of reference level) which have their centers closer than one inch or exhibit any linearity shall not be acceptable. Hash or sonic noise shall not exceed 10% of the response height of a 1/16 inch high letter I stamp at the estimated depth.

For Class II, discontinuity indications in excess of the response from a ⅛ inch high letter I die stamp at the estimated depth shall not be acceptable, and discontinuity indications in excess of 50% of the response from a ⅛ inch high letter I die stamp (50% of the reference level) which have their centers closer than one inch or exhibit a length greater than ¼ inch shall not be acceptable. Hash or sonic noise shall not exceed 20% of the response height from a ⅛ inch high letter I die stamp at the estimated depth.

For Class III, discontinuity indications in excess of the response from a 3/16 inch letter I die stamp at the estimated depth shall not be acceptable.

It should be understood that with respect to Classes I–III discussed above, Class I, or the smallest impression, provides the most critical inspection for defects, Class II an intermediate inspection, and Class III the least critical.

The specification herein discussed is not meant as a limitation on the scope of the method of the invention and its underlying theory as described in connection with the disclosed process. Various changes may be made without departing from the scope of the invention as defined in the following claims.

What is claimed as new and desired to be secured by Letters Patent of the United States is:

1. A method of inspecting critically stressed components by ultrasound comprising:
   providing an item to be inspected having a surface capable of being impressed;
   engaging the surface with a die stamp;
   impressing the surface with the die stamp in such a manner that the impression exactly conforms to the taper of said die stamp;
   subjecting the impress to ultrasound; and
   interpreting reflection of the ultrasound to determine variations from a standard.

2. A method for forming an impression profile in material used for a standard in ultrasound testing comprising the steps of:
   providing a reference standard material with a surface capable of being impressed;
   engaging the surface capable of being impressed with a die stamp;
   subjecting the die stamp to a force sufficient to impress the surface; and
   controlling the extent of impression such that said die stamp provides a repeatable impression profile of uniform shape, dimension and depth.

3. A method for forming an impression profile in material used for a standard in ultrasound testing as in claim 2 including the step of removing any upset which may have occurred on the surface of the reference standard material as a result of the step of impressing.

4. A method for forming an impression profile in material used for a standard in ultrasound testing as in claim 3 wherein the step of impressing and removing upset are repeated if necessary to obtain a precise imprint.

5. A method for forming an impression profile in material used for a standard in ultrasound testing as in claim 3 wherein the steps of impressing and upset removal are repeated until a depth control platform on the die stamp uniformly contacts the items surface to ensure impress image conformance with a standard.

6. A method for forming an impression profile in material used for a standard in ultrasound testing as in claim 3 wherein the removal of the upset is accomplished by filing.

7. A method for forming an impression profile in material used for a standard in ultrasound testing as in claim 3 wherein the step of impressing is accomplished by striking the die stamp with an inertia imparting object.

8. A method for forming an impression profile in material used for a standard in ultrasound testing as in claim 3 wherein the step of impressing includes shaping the impress to be I-shaped.

9. A method for forming an impression profile in material used for a standard in ultrasound testing as in claim 3 wherein the impress size is varied providing for different classes of inspection according to size.

10. A method for forming an impression profile in material used for a standard in ultrasound testing as in claim 3 wherein the impress depth is varied providing for different classes of inspection according to depth.

11. A method for forming an impression profile in material used for a standard in ultrasound testing as in claim 3 wherein the extent of impression is controlled by providing the die stamp with a depth control platform that determines the extent of impression when its surface area uniformly contacts the surface of the reference standard material being impressed.

* * * * *